(12) United States Patent
Unsai (10) Patent No.: US 8,602,972 B2
(45) Date of Patent: *Dec. 10, 2013

(54) IMAGE PICKUP APPARATUS AND ENDOSCOPE APPARATUS INCORPORATING THE SAME

(75) Inventor: Hiroshi Unsai, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 1275 days.

This patent is subject to a terminal disclaimer.

(21) Appl. No.: 12/423,248

(22) Filed: Apr. 14, 2009

(65) Prior Publication Data

US 2009/0259101 A1    Oct. 15, 2009

(30) Foreign Application Priority Data

Apr. 15, 2008  (JP) ................................ 2008-105976

(51) Int. Cl.
  *A61B 1/00*  (2006.01)
  *A61B 1/04*  (2006.01)
(52) U.S. Cl.
  USPC ........... 600/110; 600/109; 600/129; 600/130; 348/65; 348/340
(58) Field of Classification Search
  USPC .............. 600/109, 110, 129, 130; 359/65, 76, 359/335–340; 348/65, 76, 335–340
  See application file for complete search history.

(56) References Cited

U.S. PATENT DOCUMENTS

| | | | | |
|---|---|---|---|---|
| 4,821,117 A * | 4/1989 | Sekiguchi | ........................ | 348/68 |
| 5,014,121 A * | 5/1991 | Hasegawa et al. | .............. | 348/70 |
| 5,216,512 A * | 6/1993 | Bruijns et al. | ................. | 348/335 |
| 5,374,953 A * | 12/1994 | Sasaki et al. | ..................... | 348/65 |
| 5,577,991 A * | 11/1996 | Akui et al. | ..................... | 600/111 |
| 5,587,736 A * | 12/1996 | Walls | ............................... | 348/65 |
| 5,702,350 A * | 12/1997 | Vry et al. | ........................ | 600/166 |
| 5,751,341 A * | 5/1998 | Chaleki et al. | .................. | 348/65 |
| 5,769,792 A * | 6/1998 | Palcic et al. | ..................... | 600/477 |
| 5,772,580 A * | 6/1998 | Utsui et al. | ..................... | 600/160 |
| 5,827,190 A * | 10/1998 | Palcic et al. | ..................... | 600/476 |
| 5,910,816 A * | 6/1999 | Fontenot et al. | ................. | 348/65 |
| 7,405,877 B1 * | 7/2008 | Schechterman | .............. | 359/465 |
| 8,228,368 B2 * | 7/2012 | Zhao et al. | ....................... | 348/45 |
| 2004/0201686 A1 * | 10/2004 | Amling et al. | ............. | 348/207.1 |

(Continued)

FOREIGN PATENT DOCUMENTS

EP    0 713 672 A2    5/1996
JP    11-197097    7/1999

(Continued)

*Primary Examiner* — John P Leubecker
*Assistant Examiner* — Arnaldo Torres Diaz
(74) *Attorney, Agent, or Firm* — Scully, Scott, Murphy & Presser, P.C.

(57) ABSTRACT

An image pickup apparatus is provided with a prism unit, two solid image pickup devices, two FPCs electrically connected to the solid image pickup devices and on which an electronic component is mounted, respectively, and two communication cables for supplying power to the electronic components through the FPCs and carrying out signal transmission/receiving with the solid image pickup devices, in which a first communication cable and a second communication cable are arranged adjacently and disposed so that a line connecting a center of the first communication cable to a center of the second communication cable is in a diagonal direction of an incident face of the second solid image pickup device in a plane perpendicular to an optical axis O of an objective lens unit.

8 Claims, 7 Drawing Sheets

(56) References Cited

U.S. PATENT DOCUMENTS

| | | |
|---|---|---|
| 2005/0083536 A1* | 4/2005 | Fouquet .................. 356/512 |
| 2005/0285038 A1* | 12/2005 | Frangioni ................. 250/330 |
| 2006/0238614 A1* | 10/2006 | Konno ..................... 348/69 |
| 2007/0115376 A1* | 5/2007 | Igarashi .................. 348/262 |
| 2008/0088701 A1* | 4/2008 | Unsai et al. .............. 348/65 |
| 2008/0117324 A1* | 5/2008 | Minamio et al. ........... 348/340 |
| 2008/0180809 A1* | 7/2008 | Igarashi .................. 359/689 |
| 2009/0096894 A1* | 4/2009 | Amling et al. ............ 348/231.99 |

FOREIGN PATENT DOCUMENTS

| | | |
|---|---|---|
| JP | 2004-258497 | 9/2004 |
| JP | 2007-135951 | 6/2007 |
| JP | 2008 118568 | 5/2008 |

* cited by examiner

IMAGE PICKUP APPARATUS AND ENDOSCOPE APPARATUS INCORPORATING THE SAME

This application claims benefit of Japanese Application No. 2008-105976 filed in Japan on Apr. 15, 2008, the contents of which are incorporated by this reference.

BACKGROUND OF THE INVENTION

1. Field of the Invention

The present invention relates to an image pickup apparatus provided with two solid image pickup devices and particularly to an image pickup apparatus having two solid image pickup devices disposed at a distal end portion of an endoscope and an endoscope apparatus incorporated the same.

2. Description of the Related Art

An image pickup apparatus having an objective optical system and a solid image pickup device has been widely spread. For such an image pickup apparatus, high image quality of picked up observation images as well as size reduction depending on equipment to which the apparatus is applied are being desired.

As equipment to which the image pickup apparatus is applied is an endoscope apparatus, for example. The endoscope apparatus is provided with an insertion portion to be inserted into a body cavity, and the image pickup apparatus having an objective optical system and a solid image pickup device is disposed at a distal end portion of the insertion portion. In such an endoscope apparatus, the endoscope insertion portion is inserted into the body cavity, the image pickup apparatus in the distal end portion picks up an image of a digestive tract and the like in the body, and an operator can observe the picked up image on a monitor outside the body.

In the endoscope apparatus, a space in the distal end portion of the endoscope insertion portion is mainly occupied by the image pickup apparatus having the objective optical system and the solid image pickup device and an illumination optical system having a light guide and/or an optical device (or might further include channels depending on the type of the endoscope). Therefore, a diameter of the distal end portion of the endoscope insertion portion is substantially determined by sizes of these two members. In order to reduce the size of the image pickup apparatus, it is effective to reduce diameters of the distal end portion of the endoscope insertion portion and the insertion portion itself.

On the other hand, one of the methods to improve image quality of the image pickup apparatus is to increase the number of pixels of the solid image pickup device. However, if the number of pixels is increased, that inevitably increases the size of the solid image pickup device, and diameter reduction of the distal end portion of the endoscope insertion portion and the image quality improvement have a contradicting relation.

One of methods to solve the contradicting diameter reduction of the distal end portion and the image quality improvement is to employ a multi-plate structure in order to improve image quality by using a plurality of solid image pickup devices. The multi-plate structure used in the endoscope is suitable for an image pickup apparatus with a double-plate solid image pickup device structure (hereinafter referred to as a double-plate image pickup apparatus) using two pieces of solid image pickup devices considering the diameter reduction equivalent to a single-plate type. For example, a single-plate image pickup apparatus is provided with three types of color filters of red, green, blue or cyan, magenta, yellow in the solid image pickup device, and four pixels form a single color pixel.

On the other hand, the double-plate image pickup apparatus using two solid image pickup devices is provided with a prism applied with coating reflecting green and transmitting red and blue. In one of the two solid mage pickup devices, red and blue color filters are arranged in a stripe state in directions where red and blue are transmitted, while in the other solid image pickup device, monochromatic or green color filter is arranged in a direction where the above-mentioned green is reflected. By arranging the two solid image pickup devices as above, a pixel of each solid image pickup device forms one color pixel. Thereby, image quality can be improved by using two solid image pickup devices with fewer pixels.

Related arts of such double-plate image pickup apparatus include an image pickup apparatus for endoscope provided with two solid image pickup devices in a distal end portion of an endoscope as described in Japanese Patent Application Laid-Open Publication No. 2004-258497 and Japanese Patent Application Laid-Open Publication No. 2007-135951, for example.

In these related art double-plate image pickup apparatuses, incident light is divided into two optical paths and emitted by a prism unit in which two prisms are joined, and each of the emitted lights is received by the two solid image pickup devices so as to improve resolution of picked up observation images.

Here, by referring to FIG. 9, a configuration example of the related-art double-plate image pickup apparatus used for an endoscope will be described.

Figure 9:
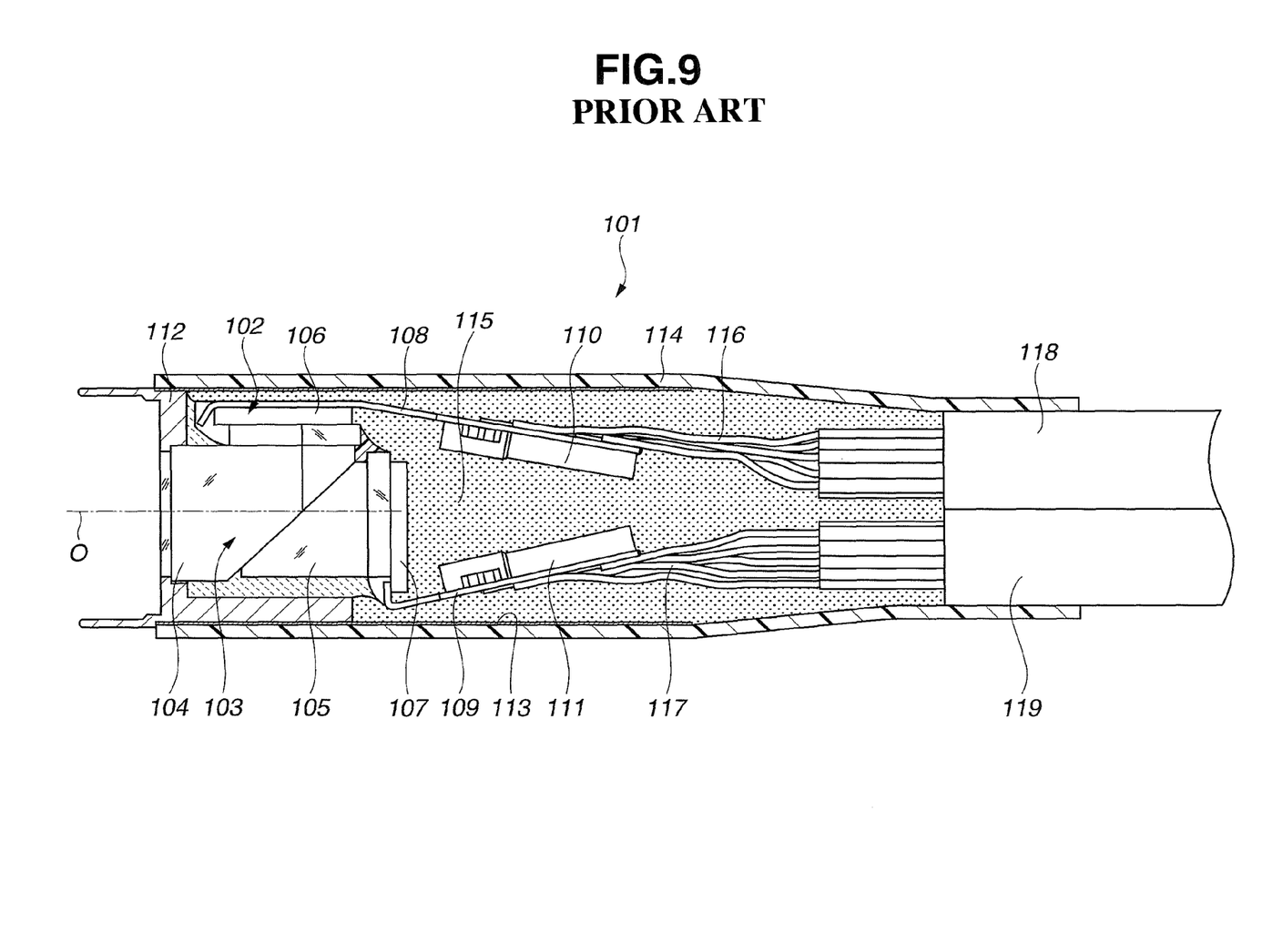
FIG. 9 is an explanatory diagram illustrating a configuration of a related-art image pickup apparatus.

As shown in FIG. 9, a double-plate image pickup apparatus 101 disposed in a distal end portion of an endoscope is provided with a prism unit 102 and two solid image pickup devices 106, 107.

The prism unit 102 has a prism portion 103 provided with a first prism 104, a second prism 105. The first solid image pickup device 106 is provided on an outgoing face side of the first prism 104, while the second solid image pickup device 107 is provided on the outgoing face side of the second prism 105.

A first FPC (flexible printed circuit board) 108 on which an electronic component 110 is mounted is connected to the first solid image pickup device 106. A plurality of signal lines 116 constituting a first communication cable 118 are electrically connected to the first FPC 108.

On the other hand, a second FPC 109 on which an electronic component 111 is mounted is connected to the second solid image pickup device 107. A plurality of signal lines 117 constituting a second communication cable 119 are electrically connected to the second FPC 109.

A distal end portion on an incident light side of the prism unit 102 is fitted and fixed in a holding holder 112. A metal frame member 113 is provided on an outer circumferential face on a proximal end side of the holding holder 112 so as to include the first and second FPCs 108, 109. A heat shrinkable tube 114 is provided on the proximal end side of the holding holder 112. The heat shrinkable tube 114 covers up to an outer circumferential portion on the distal end side of the first and second communication cables 118, 119. A filler adhesive 115 as a filler for protecting the image pickup apparatus 101 is disposed in the heat shrinkable tube 114.

As mentioned above, since the double-plate image pickup apparatus 101 has the two solid image pickup devices 106, 107 and is configured so that the two communication cables 118, 119 are electrically connected to the two solid image pickup devices 106, 107 through the FPCs 108, 109 as shown in FIG. 9, the apparatus is particularly effective in assembling performance of the image pickup apparatus.

SUMMARY OF THE INVENTION

An image pickup apparatus of an embodiment of the present invention includes: an optical unit configured by joining a first optical member and a second optical member so that incident light having passed an objective lens unit is divided into two optical paths and emitted; a first board, on which an electronic component required for driving a first solid image pickup device and electrically connected to a first solid image pickup device is mounted, the first solid image pickup device receiving light reflected by a joined surface of the first optical member and the second optical member and emitted from the optical unit and disposed so that an incident face of the light becomes parallel with an optical axis of the objective lens unit; a second board, on which an electronic component required for driving a second solid image pickup device and electrically connected to a second solid image pickup device is mounted, the second solid image pickup device receiving light transmitted through the first and second optical members and emitted from the optical unit and disposed so that an incident face of the light becomes perpendicular to the optical axis of the objective lens unit; a first cable which is electrically connected to the first board, supplies power to the electronic component through the first board and transmits/receives a signal to/from the first solid image pickup device; and a second cable which is electrically connected to the second board, supplies power to the electronic component through the second board and transmits/receives a signal to/from the second solid image pickup device, wherein the first cable and the second cable are arranged adjacently and disposed so that a line connecting a center of the first cable to a center of the second cable is in a diagonal direction of the incident face of the second solid image pickup device in a plane perpendicular to the optical axis of the objective lens unit.

The image pickup apparatus of another embodiment of the present invention includes: an optical unit configured by joining a first optical member and a second optical member so that incident light having passed an objective lens unit is divided into two optical paths and emitted; a first board, on which an electronic component required for driving a first solid image pickup device and electrically connected to a first solid image pickup device is mounted, the first solid image pickup device receiving light reflected by a joined surface of the first optical member and the second optical member and emitted from the optical unit and disposed so that an incident face of the light becomes parallel with an optical axis of the objective lens unit; a second board, on which an electronic component required for driving a second solid image pickup device and electrically connected to a second solid image pickup device is mounted, the second solid image pickup device receiving light transmitted through the first and second optical members and emitted from the optical unit and disposed so that an incident face of the light becomes perpendicular to the optical axis of the objective lens unit; a first cable which is electrically connected to the first board, supplies power to the electronic component through the first board and transmits/receives a signal to/from the first solid image pickup device; and a second cable which is electrically connected to the second board, supplies power to the electronic component through the second board and transmits/receives a signal to/from the second solid image pickup device, wherein the first cable and the second cable are arranged adjacently and disposed diagonally so that a section of the first cable and a section of the second cable are in a diagonal direction of the incident face of the second solid image pickup device in a plane perpendicular to the optical axis of the objective lens unit.

An endoscope apparatus of an embodiment of the present invention is provided with: an optical unit provided at a distal end portion of an endoscope insertion portion and configured by joining a first optical member and a second optical member so that incident light having passed an objective lens unit is divided into two optical paths and emitted; a first board, on which an electronic component required for driving a first solid image pickup device and electrically connected to a first solid image pickup device is mounted, the first solid image pickup device receiving light reflected by a joined surface of the first optical member and the second optical member and emitted from the optical unit and disposed so that an incident face of the light becomes parallel with an optical axis of the objective lens unit; a second board, on which an electronic component required for driving a second solid image pickup device and electrically connected to a second solid image pickup device is mounted, the second solid image pickup device receiving light transmitted through the first and second optical members and emitted from the optical unit and disposed so that an incident face of the light becomes perpendicular to the optical axis of the objective lens unit; a first cable which is electrically connected to the first board, supplies power to the electronic component through the first board and transmits/receives a signal to/from the first solid image pickup device; and a second cable which is electrically connected to the second board, supplies power to the electronic component through the second board and transmits/receives a signal to/from the second solid image pickup device, wherein the first cable and the second cable are arranged adjacently and disposed so that a line connecting a center of the first cable to a center of the second cable is in a diagonal direction of an incident face of the second solid image pickup device in a plane perpendicular to the optical axis of the objective lens unit.

DETAILED DESCRIPTION OF THE PREFERRED EMBODIMENTS

An embodiment of the present invention will be described below referring to the attached drawings.

In the embodiment of the present invention, description will be made below using an endoscope, which is a medical device to be inserted into a body cavity in order to observe a living tissue such as a rigid electronic endoscope provided with a rigid insertion portion, for example.

FIGS. 1 to 5 show an embodiment of an image pickup apparatus according to the present invention.

Figure 1:
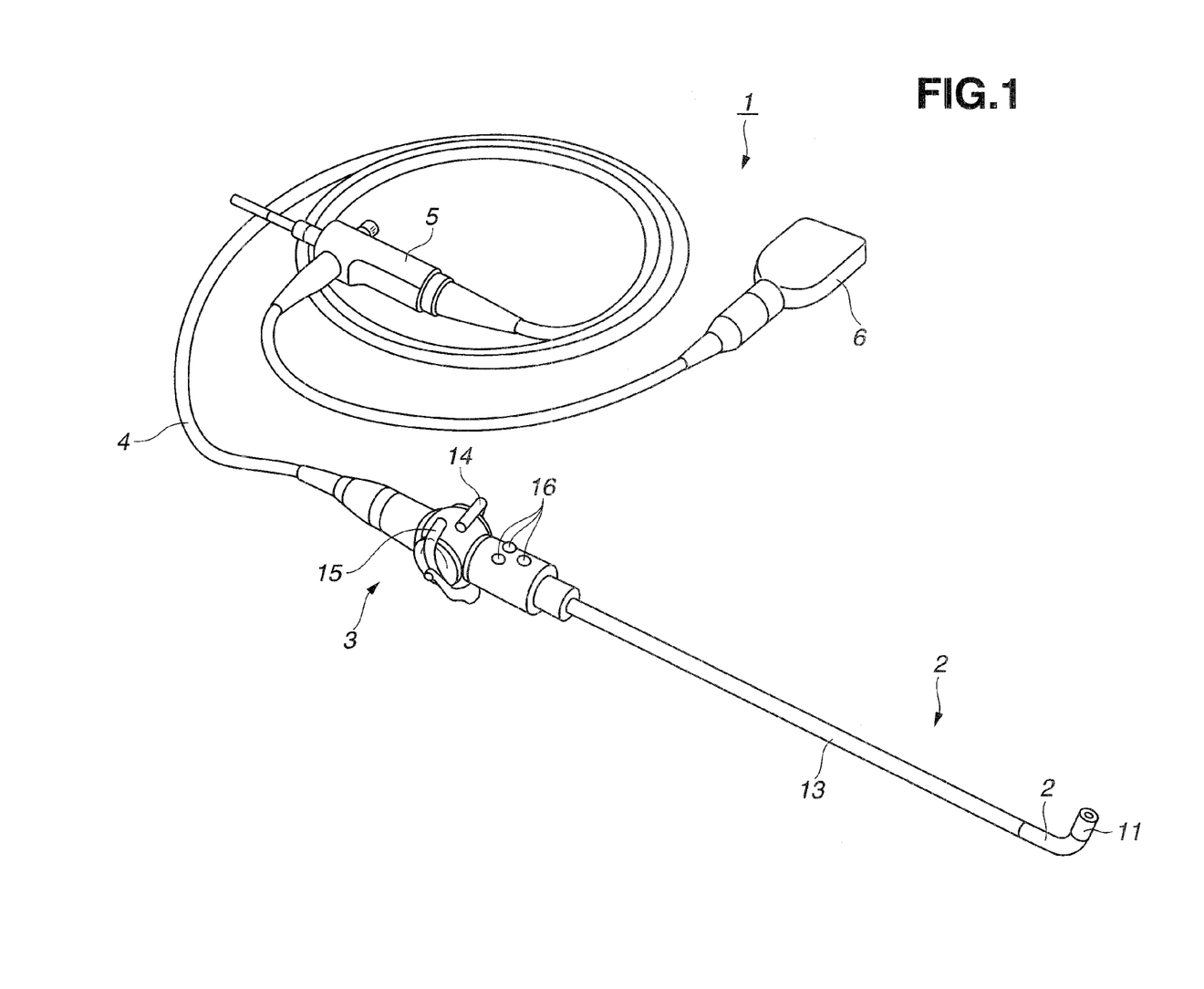
FIG. 1 shows an embodiment of an image pickup apparatus according to the present invention and is a configuration diagram illustrating an entire configuration of a rigid electronic endoscope provided with the image pickup apparatus.

A rigid electronic endoscope 1 shown in FIG. 1 (hereinafter simply referred to as an endoscope) 1 has an image pickup apparatus 51, which will be described later.

The endoscope 1 is mainly provided with an insertion portion 2, an operation portion 3 provided in a linked manner at a proximal end of the insertion portion 2, a universal cord 4 extending from the operation portion 3, a scope connector 5 disposed at the proximal end of the universal cord 4, and an electric connector 6 provided at an end portion of a cable extending from a side portion of the scope connector 5.

The insertion portion 2 of the endoscope 1 is provided with a distal end portion 11, a bending portion 12 provided in a linked manner at the distal end portion 11, and a rigid tube portion 13 provided between the bending portion 12 and the operation portion 3 in order from the distal end. The rigid tube portion 13 is formed by a rigid tube such as stainless steel, for example.

The operation portion 3 of the endoscope 1 has two bending operation levers 14, 15 for carrying out a bending operation of the bending portion 12 by a rotating operation and switches 16 for carrying out various operations. The bending operation levers 14, 15 are configured so that the bending portion 12 of the insertion portion 2 is bent vertically and horizontally by the rotating operation of an operator. Also, the plurality of switches 16 disposed at the operation portion 3 are used for operations and the like of the image pickup apparatus disposed in the distal end portion 11, for example, in predetermined endoscopic functions.

Subsequently, a structure of the distal end portion 11 of the endoscope 1 in the present embodiment will be described referring to FIG. 2.

Figure 2:
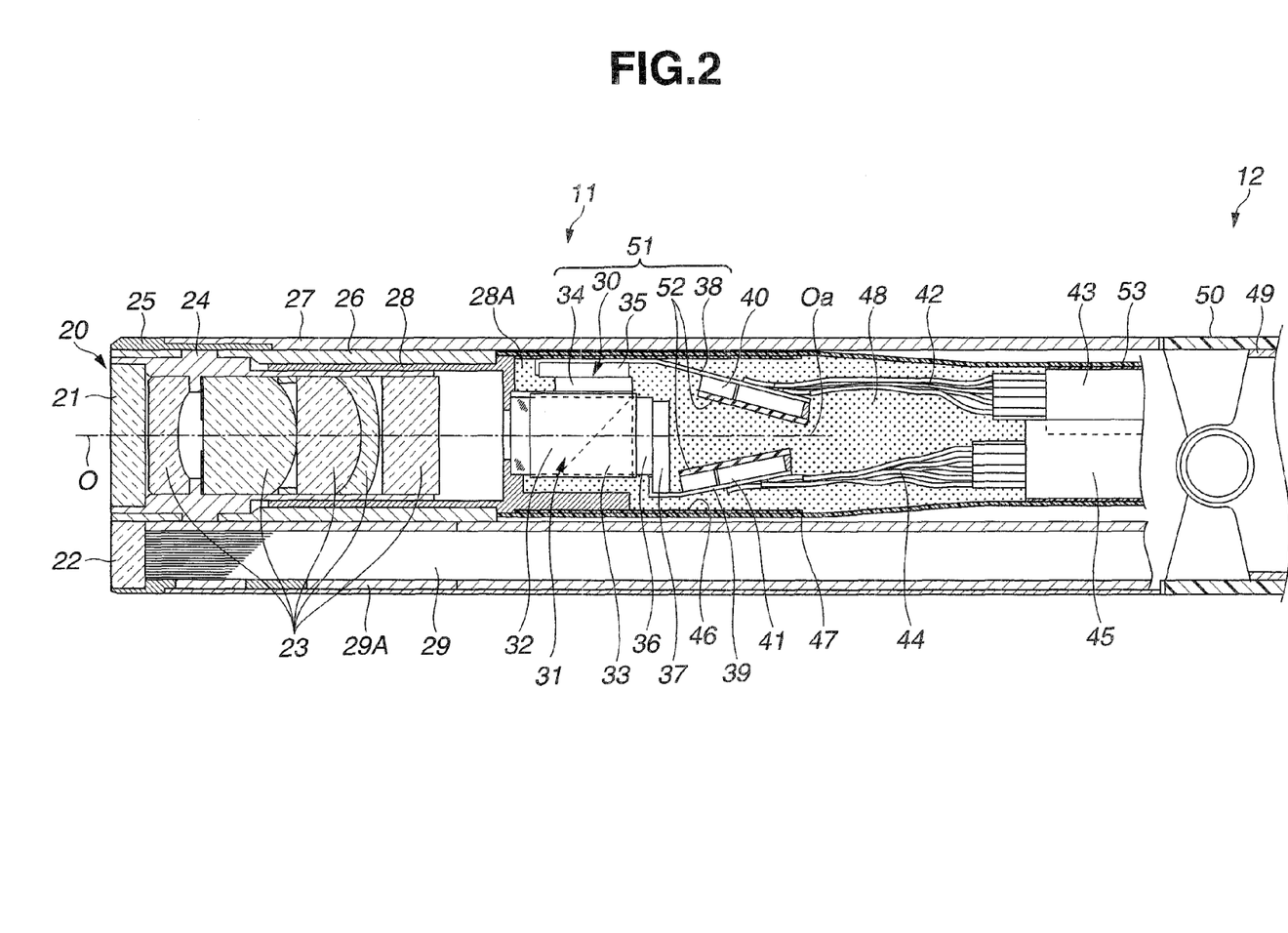
FIG. 2 is a sectional view of a distal end portion of the rigid electronic endoscope in FIG. 1.

As shown in FIG. 2, the distal end portion 11 has an observation lens 21, which is an optical member constituting an observation window, and an illumination lens 22, which is an optical member constituting an illumination window. Here, the observation lens 21 and the illumination lens 22 are disposed so that surface positions substantially match each other along a distal end surface of the distal end portion 11.

Also, the distal end portion 11 has a rigid tube 27 forming an outline so as to cover a substantially entire circumference thereof. The rigid tube 27 is fitted with a distal-end cover 25. Also, the rigid tube 27 is provided in a linked manner at the bending portion 12. The bending portion 12 is provided with a plurality of bending pieces 49 and a bending rubber 50. The bending piece 49 is formed by consecutively providing plurality of bending pieces 49 rotatably. The bending rubber 50 has flexibility and covers the plurality of bending pieces 49.

When the operator carries out the operations of the bending operation levers 14, 15 of the operation portion 3, an operation wire, not shown, is pulled/relaxed so that the bending pieces 49 are rotated to be pulled together or separated from each other, by which the bending portion 12 is bent and operated.

The observation lens 21 is held at a lens holding frame 24, together with an objective lens group 23 made up of a plurality of objective lenses.

The observation lens 21, the objective lens group 23, and the lens holding frame 24 holding them constitute an objective lens unit 20. The objective lens unit 20 is fitted and fixed to a distal end frame 26, which is a metal distal-end rigid member.

On the other hand, the illumination lens 22 is held by a distal-end cover 25. The illumination lens 22 is arranged so that the back face side thereof is opposed to a distal-end surface of a light guide bundle 29. The light guide bundle 29 is inserted through a rigid light guide holding tube 29A in the distal end portion 11. The light guide holding tube 29A is joined and fixed to the distal end frame 26.

The light guide bundle 29 is inserted through a flexible tube body (not shown) so as not to interfere with the bending operation of the bending portion 12 in the bending portion 12. The light guide bundle 29 is inserted inside the insertion portion 2, the operation portion 3, and the universal cord 4 of the endoscope 1 and disposed up to the scope connector 5. That is, the light guide bundle 29 constitutes an illumination optical transmission component that transmits illumination light from a light source device, not shown.

A holding holder 28 to be inserted through the distal end frame 26 is externally fitted and fixed to a proximal-end outer circumferential portion of the lens holding frame 24 of the objective lens unit 20. A proximal end portion of the holding holder 28 is fitted and fixed to a distal end portion of a prism unit 30 constituting the image pickup apparatus 51. The distal end portion of the prism unit 30 is the side to which incident light from the objective lens unit 20 enters.

Here, a specific configuration of the image pickup apparatus 51 of the present embodiment will be described referring to FIGS. 2 to 5.

Figure 3:
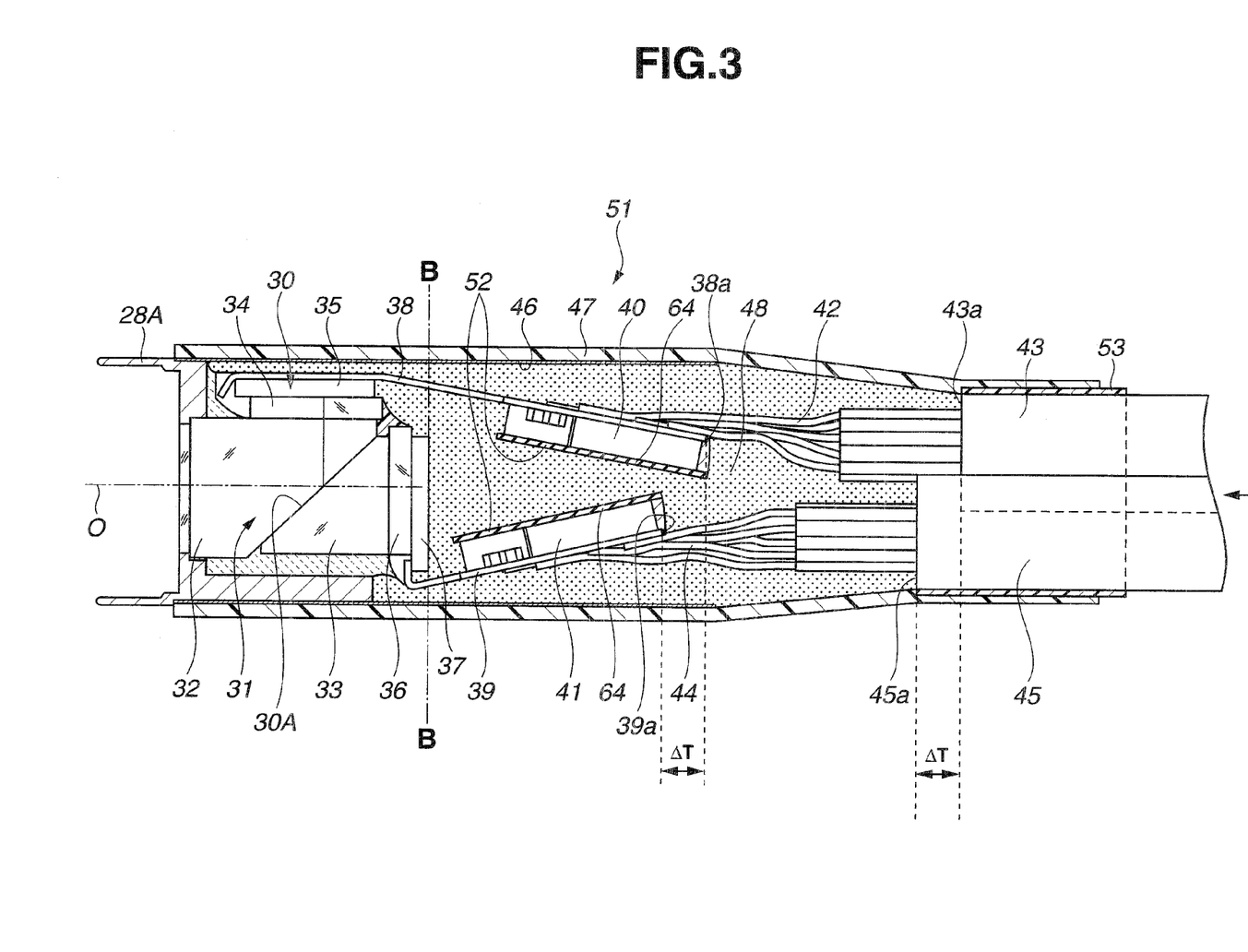
FIG. 3 is an explanatory diagram for explaining the configuration of the image pickup apparatus disposed at the distal end portion in FIG. 2.

As shown in FIGS. 2 and 3, the image pickup apparatus 51 of the present embodiment is mainly provided with the prism unit 30 as an optical unit having a prism portion 31, a first solid image pickup device 35, a second solid image pickup device 37, a first FPC 38 as a first board, a second FPC 39 as a second board, a first communication cable 43 as a first cable, and a second communication cable 45 as a second cable.

The image pickup apparatus 51 of the present embodiment constitutes a double-plate image pickup apparatus provided with the two solid image pickup devices 35, 37.

The prism portion 31 of the prism unit 30 is constituted by joining a first prism 32 as the first optical member and a second prism 33 as the second optical member and divides the incident light having passed the objective lens unit 20 into two optical paths and emits the light.

Also, the prism portion 31 is provided with a green reflection coat layer (also referred to as dichroic coat layer) 30A on a joint boundary surface where the first prism 32 and the second prism 33 are overlapped with each other.

The green reflection coat layer 30A is formed at the joint boundary surface between the first prism 32 and the second prism 33 by applying a reflection film on an inclined surface of the first prism 32 and has a characteristic to reflect green (G) light of the incident light and to transmit red (R) and blue (B) lights.

A first cover glass 34 and the first solid image pickup device 35 for reproducing a brightness signal (Y signal) are arranged in this order and bonded and fixed to each other on an outgoing face side where substantially orthogonal reflection is made by the green reflection coat layer 30A of the first prism 32.

The green light of the incident light is reflected by the green reflection coat layer 30A interposed in the joint surface between the first prism 32 and the second prism 33, emitted from the first prism 32 and received by the first solid image pickup device 35.

A second cover glass 36 and the second solid image pickup device 37 for reproducing color signals (R, B signals) are arranged in this order and bonded and fixed to each other in the rear of the outgoing face side where transmission and emission are made through the green reflection coat layer 30A of the first prism 32 and the second prism 33.

The second solid image pickup device 37 receives red and blue lights transmitted and emitted through the first prism 32 and the second prism 33.

The bonding between the first prism 32 and the second prism 33 and the bonding between the prism portion 31 and the cover glasses 34, 36 are made by bonding and fixing using an optical adhesive, for example, and carrying out a film thickness adjustment of the optical adhesive. Each position of the first solid image pickup device 35 and the second image pickup device 37 is adjusted so that an optical path length becomes the same in the case of the optical path of the first prism 32 and the case of the optical path of the second prism 33.

A light receiving surface of the second solid image pickup device 37 is provided with red (R) and blue (B) color filters installed in a stripe state, though not shown. Thereby, the second solid image pickup device 37 functions as a solid image pickup device for reproducing the color signals (R, B signals).

A color filter is not provided on the light receiving surface of the first solid image pickup device 35. Thereby, the first solid image pickup device 35 functions as a solid image pickup device for reproducing the brightness signal (Y signal).

The two solid image pickup devices 35, 37 are constituted by an image sensor such as a CCD (Charge Coupled Device) or an image sensor such as a CMOS (Complementary Metal Oxide Semiconductor). The configuration of the two solid image pickup devices 35, 37 other than presence of the color filter is substantially the same.

The two solid image pickup devices 35, 37 receive light divided by the prism portion 31 of the prism unit 30 and emitted, respectively, and photoelectrically convert the light.

Subsequently, a relation between the solid image pickup devices 35, 37 and the FPCs 38, 39 and a relation between the FPCs 38, 39 and the communication cables 43, 45 will be described referring to FIGS. 3 and 4.

As shown in FIG. 3, the first FPC (flexible printed circuit board) 38 on which an electronic component 40 such as a capacitor and an IC circuit is mounted is connected to the first solid image pickup device 35. The second FPC 39 on which an electronic component 41 such as a capacitor and an IC circuit is mounted is connected to the second solid image pickup device 37.

Also, a plurality of signal lines 42 constituting the first communication cable 43 are electrically connected to the first FPC 38. Also, a plurality of signal lines 44 constituting the second communication cable 45 are electrically connected to the second FPC 39.

The first communication cable 43 is a cable for supplying power to the electronic component 40 through the FPC 38 and carrying out signal transmission/receiving with the first solid image pickup device 35. Also, the second communication cable 45 is a cable for supplying power to the electronic component 41 through the FPC 39 and carrying out signal transmission/receiving with the second solid image pickup device 37.

As shown in FIG. 2, a metal frame member 46 is provided at a prism unit joint portion 28A of the holding holder 28 so as to include the FPCs 38, 39. Also, a heat shrinkable tube 47 is provided on an outer circumferential face of the holding holder 28. The heat shrinkable tube 47 includes the metal frame member 46 and the image pickup apparatus 51 and covers up to the distal-end side outer circumferential portions of the two communication cables 43, 45.

A heat shrinkable tube 53 separate from the heat shrinkable tube 47 is provided between the distal-end side outer circumferential portions of the two communication cables 43, 45 and the heat shrinkable tube 47. The heat shrinkable tube 53 is formed using a synthetic resin such as polyolefin (thermoplastic plastic), for example. The heat shrinkable tube 53 is provided at the distal-end side outer circumferential portions of the two communication cables 43, 45 covered by the heat shrinkable tube 47.

As mentioned above, since the heat shrinkable tube 53 is provided at the distal-end side outer circumferential portions of the two communication cables 43, 45 covered by the heat shrinkable tube 47, close adhesion and adhesion strength between the distal-end side portions of the two communication cables 43, 45 and the heat shrinkable tube 47 are improved.

If autoclave sterilization (high-pressure steam sterilization) treatment is applied to the related-art image pickup apparatus in which a plurality of communication cables are extended, sheathes of the plurality of cables are displaced, and there is a fear that signal transmission/receiving is badly influenced.

However, since the close adhesion and adhesion strength between the heat shrinkable tube 47 and the two communication cables 43, 45 are improved by the heat shrinkable tube 53 in the image pickup apparatus 51 of the present embodiment, the sheathes of the communication cables 43, 45 are not removed even if the autoclave sterilization is applied, and resistance against the autoclave sterilization can be improved.

The configuration in which the heat shrinkable tube 53 is provided at the distal-end side outer circumferential portions of the two communication cables 43, 45 covered by the heat shrinkable tube 47 has been described, but not limited to that, the tube may be configured to be provided over the entire longitudinal directions of the two communication cables 43, 45.

A filler adhesive 48, which is filler for protecting the image pickup apparatus 51, is disposed in the heat shrinkable tube 47.

Figure 4:
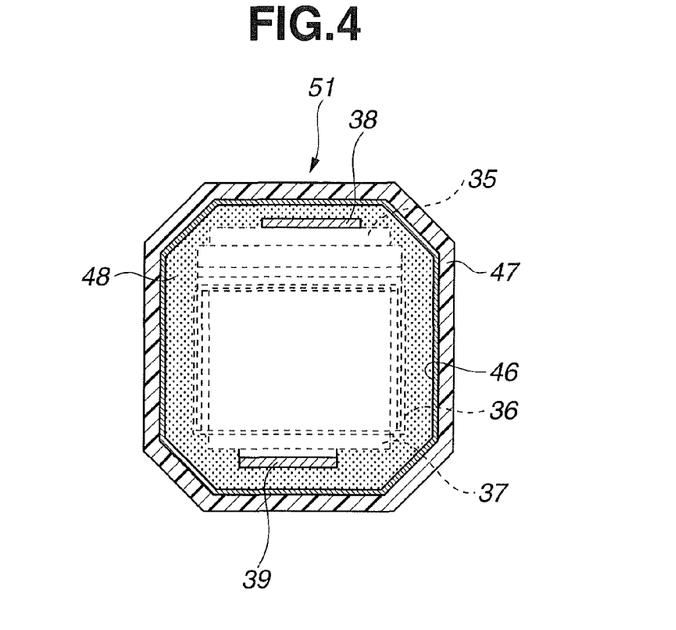
FIG. 4 is a B-B line sectional view of FIG. 3, illustrating a state where a coagulation adhesive in the image pickup apparatus is provided evenly.

The filler adhesive 48 may be provided and fixed evenly at right and left regions between the metal frame member 46 and the second solid image pickup device 37 in the image pickup apparatus 51 and upper and lower regions between the metal frame member 46 and the first and second FPCs 38, 39, respectively, as shown in a sectional view (B-B line sectional view in FIG. 3) of the image pickup apparatus 51 in the vicinity of the second solid image pickup device 37 in FIG. 4, for example. As a result, the second solid image pickup device 37 which occupies a large area in a plane perpendicular to an optical axis O of the objective lens unit 20 can be arranged in the vicinity of the center of the image pickup apparatus 51, which contributes to size and diameter reduction of the image pickup apparatus 51.

Also, the image pickup apparatus 51 is provided with an insulating member 52 for preventing contact between the electronic components 40, 41 and insulating them on each diagonal face of the electronic components 40, 41. The insulating member 52 is provided on an entire region or a part thereof on an extension line Oa side of the optical axis O of the objective lens unit 20 in opposing surfaces of the electronic components 40, 41 mounted on the FPCs 38, 39, respectively.

The insulating member 52 is an insulating tape formed by an insulating material, for example, and affixed to the entire regions or a part of the regions of the electronic components 40, 41 opposed to the extension line Oa of the optical axis O, respectively. The insulating member 52 is not limited to the insulating tape but may be an insulating layer formed by applying a fluid insulating material on the entire regions or a part of the regions of the electronic components 40, 41, for example.

As mentioned above, since the contact between the electronic component 40 and the electronic component 41 can be prevented by providing the insulating member 52 on the entire region or a part thereof of the electronic components 40, 41 mounted on the FPCs 38, 39, respectively, opposed to the extension line Oa of the optical axis O, the electronic components 40, 41 are not short-circuited but operations of the electronic components 40, 41 and the solid image pickup devices 35, 37 can be stabilized.

In the present embodiment, the two FPCs 38, 39 have the electronic components 40, 41 disposed oppositely to each other (facing each other) with the extension line Oa of the optical axis O of the objective lens unit 20 between them; however, not limited to such an arrangement mode, it is only necessary that the two communication cables 43, 45 are arranged at positions electrically connectable. But, when component arrangement structures and assembling performance improvement suitable for size reduction of the image pickup apparatus 51 are considered, the two FPCs 38, 39 are preferably configured so that the electronic components 40, 41 are opposed to each other with the extension line Oa of the optical axis O of the objective lens unit 20 between them as in the present embodiment.

Subsequently, the configuration of a major part of the image pickup apparatus 51 of the present embodiment will be described referring to FIG. 5.

Figure 5:
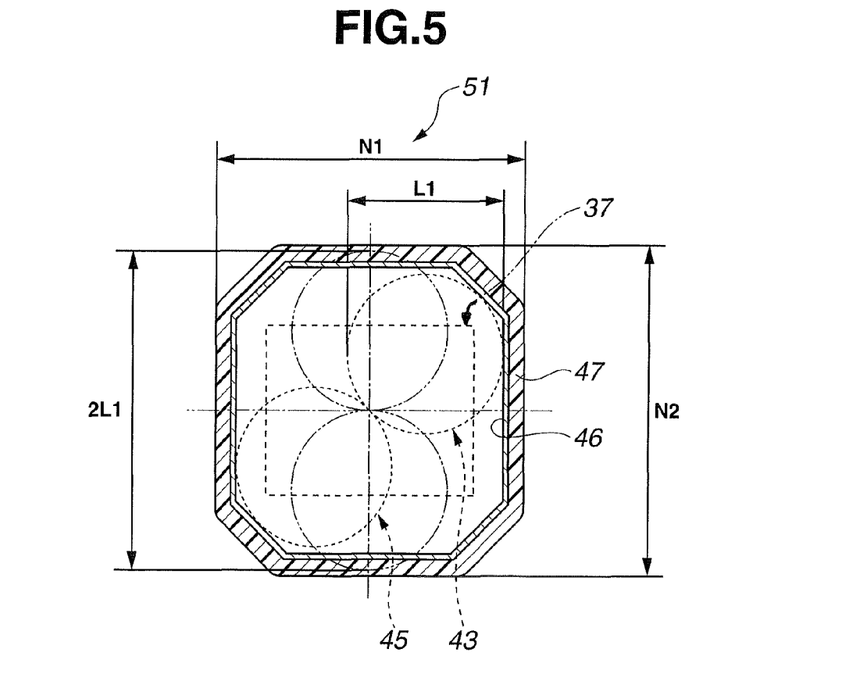
FIG. 5 is an explanatory diagram for explaining a configuration of a case seen from an arrow direction A in FIG. 3.

The image pickup apparatus 51 of the present embodiment is configured, as shown in FIG. 5, such that the first communication cable 43 and the second communication cable 45 are arranged adjacently and disposed so that the line connecting the center of the first communication cable 43 and the center of the second communication cable 45 is in a diagonal direction of the incident face of the second solid image pickup device 37 in the plane perpendicular to the optical axis O of the objective lens unit 20.

In the configuration example shown in FIG. 5, the first communication cable 43 is arranged upper right in the image pickup apparatus 51 in the plane perpendicular to the optical axis O of the objective lens unit 20, the second communication cable 45 is arranged lower left in the image pickup apparatus 51, and the two communication cables 43, 45 are disposed such that the centers of the cables are in the diagonal direction of the incident face of the second solid image pickup device 37 and sandwich the optical axis O.

The arrangement of the two communication cables 43, 45 is not limited to the arrangement mode shown in FIG. 5.

For example, it may be so configured that the first communication cable 43 is arranged upper left in the image pickup apparatus 51 in the plane perpendicular to the optical axis O of the objective lens unit 20, the second communication cable 45 is arranged lower right in the image pickup apparatus 51 in conformity to the positions of the two FPCs 38, 39 and disposed such that the centers of the two communication cables 43, 45 are in the diagonal direction of the incident face of the second solid image pickup device 37 and sandwich the optical axis O.

Here, an action of the image pickup apparatus 51 constituting the major part as above will be described referring to FIG. 5.

As shown in FIG. 5, in the image pickup apparatus 51 of the present embodiment, suppose that an outer diameter of the image pickup apparatus 51 in a horizontal direction of the plane perpendicular to the optical axis O of the objective lens unit 20 is N1, the outer diameter of the image pickup apparatus 51 in a vertical direction is N2, and a width dimension of each of the two communication cables 43, 45 (shown by a broken line in FIG. 5) is L1, for example.

In this case, in the present embodiment, the two communication cables 43, 45 constituted by the width dimension L1, respectively, are configured to be disposed such that the line connecting the center of the first communication cable 43 and the center of the second communication cable 45 is in the diagonal direction of the incident face of the second solid image pickup device 37, they are accommodated in the image pickup apparatus 51 (in an inner diameter of the image pickup apparatus 51) constituted by the dimension N1 and the dimension N2.

However, as shown by a two-dotted broken line in FIG. 5, suppose that the two communication cables 43, 45 are disposed side by side in the vertical direction in the plane perpendicular to the optical axis O of the objective lens unit.

Then, the width dimension 2L1 of the two communication cables 43, 45 in the vertical direction becomes larger than the inner diameter of the image pickup apparatus 51 of the present embodiment in the vertical direction. That is, if the two communication cables 43, 45 are disposed side by side in the vertical direction in the plane perpendicular to the optical axis O of the objective lens, the dimension N2 of the image pickup apparatus 51 should be increased so as to accommodate the two communication cables 43, 45 having the width dimension 2L1.

However, in the present embodiment, the two communication cables 43, 45 having the width dimension of 2L1 can be accommodated in the image pickup apparatus 51 with the dimensions N2, N1. Thus, it is obvious that the arrangement configuration of the communication cables 43, 45 as shown in FIG. 5 is a configuration suitable for size reduction in the image pickup apparatus 51 having the two communication cables 43, 45.

Therefore, according to the present embodiment, since the size and diameter reduction of the image pickup apparatus 51 can be realized by disposing the two communication cables 43, 45 to be in the diagonal direction of the incident face of the second solid image pickup device 37, great contribution can be made to the diameter reduction of the distal end portion 11 of the endoscope 2.

Here, the image pickup apparatus 51 of the present embodiment is applied with improvement suitable for size reduction and improvement for assembling performance improvement along with the arrangement configuration of the two communication cables 43, 45 as above. Such variations will be described referring to FIGS. 3, 6A to 8.

(Variation)

Figure 6A:
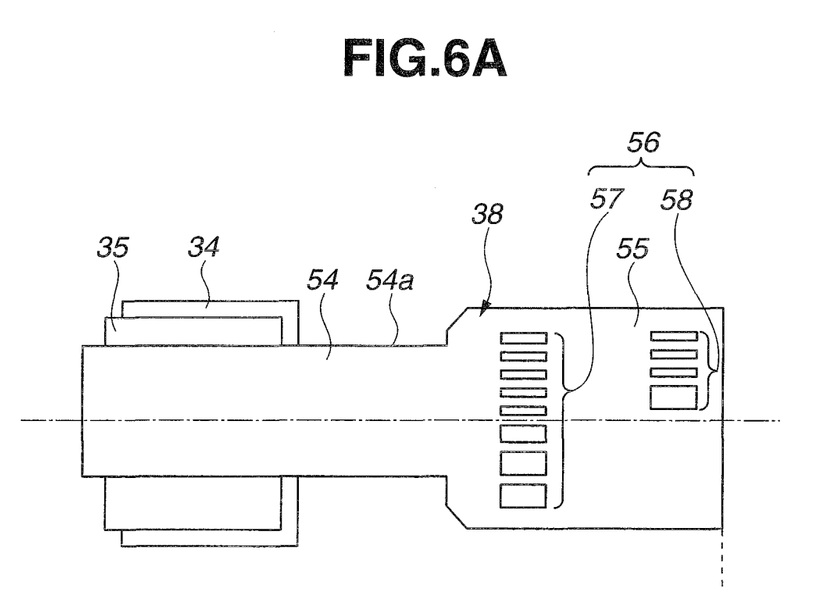
FIGS. 6A and 6B are diagrams for explaining a configuration of two FPCs provided at the image pickup apparatus in FIG. 3.
Figure 6B:
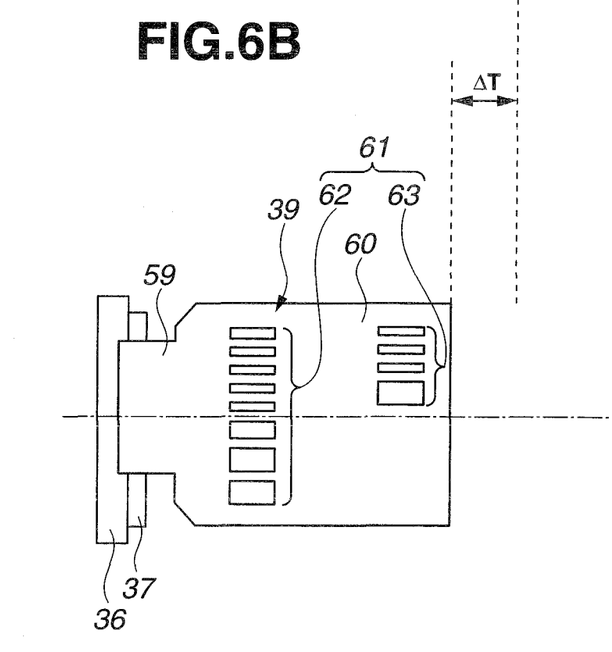
Figure 7:
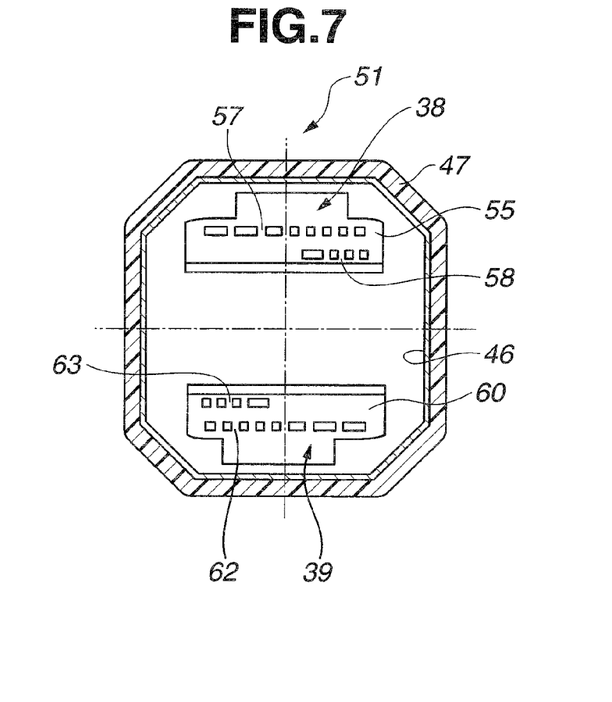
FIG. 7 is an explanatory diagram for explaining an arrangement configuration of the two FPCs when seen from the arrow direction A in FIG. 3.
Figure 8:
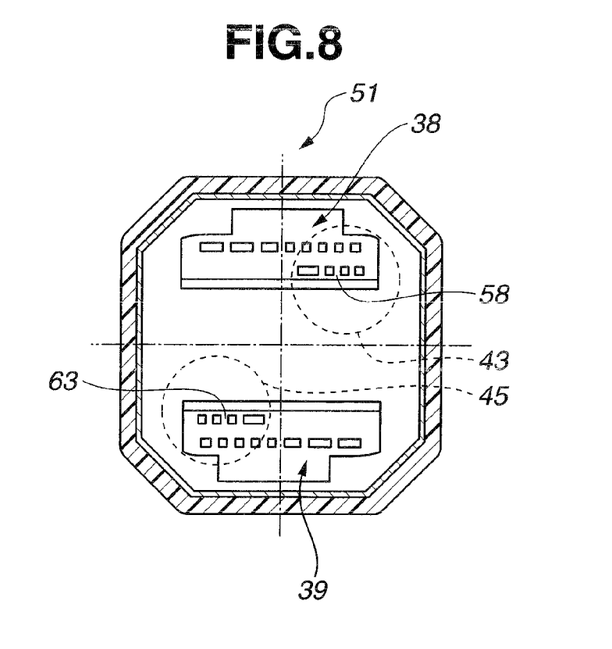
FIG. 8 is an explanatory diagram for explaining an arrangement configuration of the two FPCs and two communication cables in FIG. 7.

FIGS. 6A and 6B explain the configurations of the two FPCs provided in the image pickup apparatus in FIG. 3, in which FIG. 6A is a top view of the first FPC, FIG. 6B is a bottom view of the second FPC, FIG. 7 is an explanatory diagram for explaining an arrangement configuration of the two FPCs when seen from the arrow direction A in FIG. 3, and FIG. 8 is an explanatory diagram for explaining the arrangement configuration of the two FPCs and the two communication cables in FIG. 7.

As shown in FIG. 3, the first communication cable 43 and the second communication cable 45 have respective distal end portions 43a, 45a from which the plurality of signal lines 42, 44 are exposed, and the distal end portions 43a, 45a are disposed at positions displaced in the direction of the optical axis O of the objective lens unit 20.

The first FPC 38 and the second FPC 39 are disposed according to the positions displaced in the optical axis O direction of the objective lens unit 20 of the first communication cable 43 and the second communication cable 45.

Specifically, as shown in FIG. 3, a proximal end portion 38a of the FPC 38 on the communication cable 43 side is disposed at a position displaced by a distance ΔT set in advance in a direction of an extension line Oa of the optical axis O of the objective lens unit 20 from a proximal end portion 39a of the FPC 39 on the communication cable 45 side.

In this case, the distal end portion 43a of the communication cable 43 is disposed at a position displaced by the distance ΔT set in advance in the direction of the extension line Oa of the optical axis O of the objective lens unit 20 from the distal end portion 45a of the communication cable 45.

In conformity to the displacement of the respective distal end portions 43a, 45a of the two communication cables 43, 45, a length of an extending direction of the first FPC 38 is configured to become longer than the length of the extending direction of the second FPC 39.

FIGS. 6A and 6B show specific configurations of the two FPCs 38, 39.

The first FPC 38 is, as shown in FIG. 6A, provided with a connection portion 54 to be connected to the solid image pickup device 35 and a board main body portion 55 formed by extending the connection portion 54. The connection portion 54 is formed with a width narrower than the width of the board main body portion 55, and a gripping portion 54a for handling with a jig and the like in assembly is provided on both sides between a portion not connected to the solid image pickup device 35 and an extended portion of the board main body portion 55.

A connection land portion 56 is provided on an upper face of the board main body portion 55. The connection land portion 56 is provided with a first connection land 57 and a second connection land 58. The second connection land 58 is, as shown in FIG. 7, disposed in a right side direction in a plane perpendicular to the optical axis O of the objective lens unit 20. A plurality of signal lines 42 of the first communication cable 43 are connected and fixed to the two connection lands 57, 58, respectively, by solder and the like.

On the other hand, the second FPC 39 is provided with a connection portion 59 to be connected to the solid image pickup device 37 and a board main body portion 60 formed by extending the connection portion 59. The connection portion 59 is connected to the solid image pickup device 37 in a state in which a proximal end portion is bent and is formed so that a length in the extending direction is shorter than the connection portion 54 of the FPC 38.

A connection land portion 61 is provided on a lower face of the board main body portion 60. The connection land portion 61 is provided with a first connection land 62 and a second connection land 63. The second connection land 63 is, as shown in FIG. 7, disposed in a left side direction in the plane perpendicular to the optical axis O of the objective lens unit 20. A plurality of signal lines 44 of the second communication cable 45 are connected and fixed to the two connection lands 62, 63, respectively, by solder and the like.

As mentioned above, each of the second connection lands 58, 63 of the two FPCs 38, 39 is arranged with bias in directions different from each other in the plane perpendicular to the optical axis O as shown in FIGS. 7 and 8. Each direction where each of the second connection lands 58, 63 is arranged corresponds to a direction of an arrangement position of the two communication cables 43, 45.

That is, since each of the second connection lands 58, 63 of the two FPCs 38, 39 is arranged in the direction corresponding to the directions of the arrangement positions of the two communication cables 43, 45, a work in a connecting process can be facilitated.

Also, the two FPCs 38, 39 are, as shown in FIGS. 3 and 7, fixed and held by the filler adhesive 48 in a state in which they are bent to the extension line Oa side of the optical axis O of the objective lens unit 20.

Here, when an attention is paid to configurations of the two communication cables 118, 119 in the related art example, in the related art example shown in FIG. 9, the distal end portions of the two communication cables 118, 119 are disposed at the same positions with respect to an optical axis direction of the objective lens unit (optical axis extension line direction), and there is a fear that the two communication cables 118, 119 might be short-circuited.

However, in the present embodiment, since the distal end portion 43a of the communication cable 43 is disposed at a position displaced by the distance ΔT set in advance in the extension line Oa direction of the optical axis O of the objective lens unit 20 from the distal end portion 45a of the communication cable 45, the short-circuit between the two communication cables 43, 45 can be prevented.

The proximal end portion 38a of the FPC 38 on the communication cable 43 side is disposed at a position displaced by the distance ΔT set in advance in the extension line Oa direction of the optical axis O of the objective lens unit 20 from the proximal end portion 39a of the FPC 39 on the communication cable 45 side, and moreover, since the second connection lands 58, 63 of the FPCs 38, 39 are arranged in the different directions corresponding to the directions of the arrangement positions of the two communication cables 43, 45, contact between the two communication cables 43, 45 and short-circuit between the connection lands 58, 63 can be also prevented.

If the distal end portion of the image pickup apparatus is in a structure provided with the two FPCs 38, 39 connected to the two solid image pickup devices 35, 37, there is a fear that the proximal end portions 38a, 39a of the two FPCs 38, 39 or the connection land portions 56, 61 might interfere with the metal frame member 46.

However, in the present embodiment, since the two FPCs 38, 39 are fixed and held by the filler adhesive 48 in the state bent on the extension line Oa side of the optical axis O of the objective lens unit 20 as shown in FIGS. 3 and 8, the proximal end portions 38a, 39a of the FPCs 38, 39 do not get close to the metal frame member 46, thereby occurrence of interference can be prevented.

Here, the assembling process of the image pickup apparatus 51 will be described. After the second FPC 39 is connected and fixed to the solid image pickup device 37, the first FPC 38 is connected and fixed to the first solid image pickup device 35, while the gripping portion 54a of the first FPC 38 is handled using a jig and the like.

In this case, since the gripping portion 54a is provided at the first FPC 38, an operator can easily mount the FPC 38 on the solid image pickup device 35 by handling the gripping portion 54a with the jig and the like. Moreover, since the connection portion 54 having the gripping portion 54a is formed long in the extension direction, the operator can easily bend the FPC 38 on the extension line Oa side of the optical axis O of the objective lens unit 20.

After that, the operator fills the filler adhesive 48 in the heat shrinkable tube 47 so that the two FPCs 38, 39 are fixed and held in the state bent on the extension line Oa side of the optical axis O of the objective lens unit 20 as shown in FIGS. 3 and 7.

Therefore, according to such a variation, since the distal end portion 43a of the communication cable 43 is disposed at the position displaced by the distance ΔT set in advance in the extension line Oa direction of the optical axis O of the objective lens unit 20 from the distal end portion 45a of the communication cable 45, the short-circuit between the two communication cables 43, 45 can be prevented.

Also, since the two FPCs 38, 39 are fixed and held by the filler adhesive 48 in the state bent on the extension line Oa side of the optical axis O of the objective lens unit 20, the proximal end portions 38a, 39a of the FPCs 38, 39 do not get close to the metal frame member 46 but occurrence of interference can be prevented.

Moreover, since the gripping portion 54a is provided at the first FPC 38, the operator can easily mount the FPC 38 to the solid image pickup device 35 by handling the gripping portion 54a with the jig and the like. Also, since the connection portion 54 having the gripping portion 54a is formed long in the extension direction, the operator can easily bend the FPC 38 on the extension line Oa side of the optical axis O of the objective lens unit 20. Thus, the assembling performance of the image pickup apparatus 51 is improved.

The invention described in each of the embodiments above is not limited to the embodiments and variations but is capable of various deformation within a range not departing from the gist thereof in a stage of being put into practice. Moreover, the above embodiments include the invention in various stages, and the various inventions can be extracted by appropriate combinations in a plurality of disclosed constituent requirements.

For example, even if some constituent requirements are deleted from all the constituent requirements shown in the embodiments, if the problem to be solved by the invention can be solved and the described effect can be obtained, the configuration from which the constituent requirements have been deleted can be extracted as the invention.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An image pickup apparatus comprising:
   an optical unit configured by joining a first optical member and a second optical member so that incident light having passed an objective lens unit is divided into two optical paths and emitted;
   a first board, on which an electronic component required for driving a first solid image pickup device and electrically connected to a first solid image pickup device is mounted, the first solid image pickup device receiving light reflected by a joined surface of the first optical member and the second optical member and emitted from the optical unit and disposed so that an incident face of the light becomes parallel with an optical axis of the objective lens unit;
   a second board, on which an electronic component required for driving a second solid image pickup device and electrically connected to a second solid image pickup device is mounted, the second solid image pickup device receiving light transmitted through the first and second optical members and emitted from the optical unit and disposed so that an incident face of the light becomes perpendicular to the optical axis of the objective lens unit
   a first cable which is electrically connected to the first board, supplies power to the electronic component through the first board and transmits/receives a signal to/from the first solid image pickup device; and
   a second cable which is electrically connected to the second board, supplies power to the electronic component through the second board and transmits/receives a signal to/from the second solid image pickup device,
   wherein the first cable and the second cable are arranged to be adjacent and disposed so that a line connecting a center of the first cable and a center of the second cable in a plane perpendicular to the optical axis of the objective lens unit is in a diagonal direction of the incident face of the second solid image pickup device,
   wherein the first board and the second board are disposed so that the electronic component mounted on the first substrate and the electronic component mounted on the second substrate are opposed with an extension line of the optical axis of the objective lens unit therebetween, and disposed to be displaced in a direction of the optical axis of the objective lens unit,
   wherein the first cable and the second cable have a plurality of signal lines electrically connected to the first and second boards, respectively, inside, and respective distal end portions having the signal lines exposed are disposed at positions displaced in the direction of the optical axis of the objective lens unit, and
   wherein the first board and the second board are disposed corresponding to the displaced positions of the first cable and the second cable in the direction of the optical axis of the objective lens unit.

2. The image pickup apparatus according to claim 1, wherein if a proximal end portion of the first board on a first cable side is disposed at a position displaced by a distance set in advance in the direction of the optical axis of the objective lens unit from a proximal end portion of the second board on a second cable side, the distal end portion of the first cable is disposed at a position displaced by the distance set in advance in the direction of the optical axis of the objective lens unit from the distal end portion of the second cable.

3. The image pickup apparatus according to claim 1, wherein a length of the first board in an extending direction in which a proximal end portion on a first cable side extends toward the distal end portion of the first cable is longer than a length of the second board in an extending direction in which a proximal end portion on a second cable side extends toward the distal end portion of the second cable.

4. The image pickup apparatus according to claim 2, wherein a length of the first board in an extending direction in which the proximal end portion on the first cable side extends toward the distal end portion of the first cable is longer than a length of the second board in an extending direction in which the proximal end portion on the second cable side extends toward the distal end portion of the second cable.

5. The image pickup apparatus according to claim 1, wherein
the first board has a connection land portion for electrically connecting the plurality of signal lines of the first cable, and the second board has a connection land portion for electrically connecting the plurality of signal lines of the second cable, the connection land portion of the first board and the connection land portion of the second board being provided at positions corresponding to the positions of the first cable and the second cable and disposed with bias so as to be in a diagonal direction of an incident face of the second solid image pickup device in a plane perpendicular to the optical axis of the objective lens unit.

6. The image pickup apparatus according to claim 5, wherein the connection land portion of the first board and the connection land portion of the second board are provided on a plane of the respective boards on which the electronic component is not mounted.

7. An image pickup apparatus comprising:
an optical unit configured by joining a first optical member and a second optical member so that incident light having passed an objective lens unit is divided into two optical paths and emitted;
a first board, on which an electronic component required for driving a first solid image pickup device and electrically connected to a first solid image pickup device is mounted, the first solid image pickup device receiving light reflected by a joined surface of the first optical member and the second optical member and emitted from the optical unit and disposed so that an incident face of the light becomes parallel with an optical axis of the objective lens unit;
a second board, on which an electronic component required for driving a second solid image pickup device and electrically connected to a second solid image pickup device is mounted, the second solid image pickup device receiving light transmitted through the first and second optical members and emitted from the optical unit and disposed so that an incident face of the light becomes perpendicular to the optical axis of the objective lens unit;
a first cable which is electrically connected to the first board, supplies power to the electronic component through the first board and transmits/receives a signal to/from the first solid image pickup device; and
a second cable which is electrically connected to the second board, supplies power to the electronic component through the second board and transmits/receives a signal to/from the second solid image pickup device,
wherein the first cable and the second cable are arranged adjacently and disposed diagonally so that a section of the first cable and a section of the second cable in a plane perpendicular to the optical axis of the objective lens unit are in a diagonal direction of the incident face of the second solid image pickup device,
wherein the first board and the second board are disposed so that the electronic component mounted on the first substrate and the electronic component mounted on the second substrate are opposed with an extension line of the optical axis of the objective lens unit therebetween, and disposed to be displaced in a direction of the optical axis of the objective lens unit,
wherein the first cable and the second cable have a plurality of signal lines electrically connected to the first and second boards, respectively, inside, and respective distal end portions having the signal lines exposed are disposed at positions displaced in the direction of the optical axis of the objective lens unit, and
wherein the first board and the second board are disposed corresponding to the displaced positions of the first cable and the second cable in the direction of the optical axis of the objective lens unit.

8. An endoscope apparatus comprising:
an optical unit provided at a distal end portion of an endoscope insertion portion and configured by joining a first optical member and a second optical member so that incident light having passed an objective lens unit is divided into two optical paths and emitted;
a first board, on which an electronic component required for driving a first solid image pickup device and electrically connected to a first solid image pickup device is mounted, the first solid image pickup device receiving light reflected by a joined surface of the first optical member and the second optical member and emitted from the optical unit and disposed so that an incident face of the light becomes parallel with an optical axis of the objective lens unit;
a second board, on which an electronic component required for driving a second solid image pickup device and electrically connected to a second solid image pickup device is mounted, the second solid image pickup device receiving light transmitted through the first and second optical members and emitted from the optical unit and disposed so that an incident face of the light becomes perpendicular to the optical axis of the objective lens unit;
a first cable which is electrically connected to the first board, supplies power to the electronic component through the first board and transmits/receives a signal to/from the first solid image pickup device; and
a second cable which is electrically connected to the second board, supplies power to the electronic component through the second board and transmits/receives a signal to/from the second solid image pickup device,
wherein the first cable and the second cable are arranged to be adjacent and disposed so that a line connecting a center of the first cable and a center of the second cable in a plane perpendicular to the optical axis of the objective lens unit is in a diagonal direction of the incident face of the second solid image pickup device,
wherein the first board and the second board are disposed so that the electronic component mounted on the first substrate and the electronic component mounted on the second substrate are opposed with an extension line of the optical axis of the objective lens unit therebetween, and disposed to be displaced in a direction of the optical axis of the objective lens unit,
wherein the first cable and the second cable have a plurality of signal lines electrically connected to the first and second boards, respectively, inside, and respective distal end portions having the signal lines exposed are disposed at positions displaced in the direction of the optical axis of the objective lens unit, and
wherein the first board and the second board are disposed corresponding to the displaced positions of the first cable and the second cable in the direction of the optical axis of the objective lens unit.

* * * * *